(12) United States Patent  
Jones

(10) Patent No.: US 8,515,555 B1  
(45) Date of Patent: Aug. 20, 2013

(54) EXTENSION DEVICE FOR COUPLING BETWEEN PULSE GENERATOR AND STIMULATION LEAD, STIMULATION SYSTEM USING THE SAME, AND METHOD OF MANUFACTURING THE SAME

(75) Inventor: Robert E. Jones, McKinney, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 840 days.

(21) Appl. No.: 12/247,531

(22) Filed: Oct. 8, 2008

Related U.S. Application Data

(60) Provisional application No. 60/978,592, filed on Oct. 9, 2007.

(51) Int. Cl.
*A61N 1/00* (2006.01)

(52) U.S. Cl.
USPC .......................................... 607/115

(58) Field of Classification Search
USPC .................................... 607/115, 2
See application file for complete search history.

(56) References Cited

U.S. PATENT DOCUMENTS

| | | | |
|---|---|---|---|
| 6,671,554 B2 | 12/2003 | Gibson et al. | |
| D523,557 S | 6/2006 | Jones et al. | |
| 7,425,142 B1* | 9/2008 | Putz | 439/138 |
| 7,539,542 B1 | 5/2009 | Malinowski | |
| 7,594,828 B2 | 9/2009 | Alexander et al. | |
| 7,794,256 B1* | 9/2010 | Sochor | 439/289 |
| 2005/0027327 A1* | 2/2005 | Ries et al. | 607/37 |
| 2005/0137665 A1 | 6/2005 | Cole | |
| 2006/0168805 A1* | 8/2006 | Hegland et al. | 29/854 |
| 2007/0168007 A1* | 7/2007 | Kuzma et al. | 607/116 |
| 2008/0208301 A1* | 8/2008 | Alexander et al. | 607/116 |

* cited by examiner

*Primary Examiner* — Niketa Patel
*Assistant Examiner* — Minh Duc Pham

(57) ABSTRACT

In one embodiment, a lead extension comprises: a lead body; a plurality of conductors disposed within the lead body; a plurality of terminal contacts on a proximal end of the lead body, wherein the plurality of terminal contacts are electrically coupled to the plurality of conductors; and a housing structure disposed at a distal end of the lead body, the housing structure enclosing a plurality of electrical connectors for making electrical contact with terminal contacts of a stimulation lead, wherein the plurality of electrical connectors are electrically coupled to the plurality of conductors; the housing structure comprising an outer body of a first material and an inner reinforcing structure of a second material, wherein the first material is a relatively pliable biocompatible polymer material and the second material is a relatively rigid material, the reinforcing structure holding the plurality of electrical connectors in a relatively fixed arrangement.

14 Claims, 3 Drawing Sheets

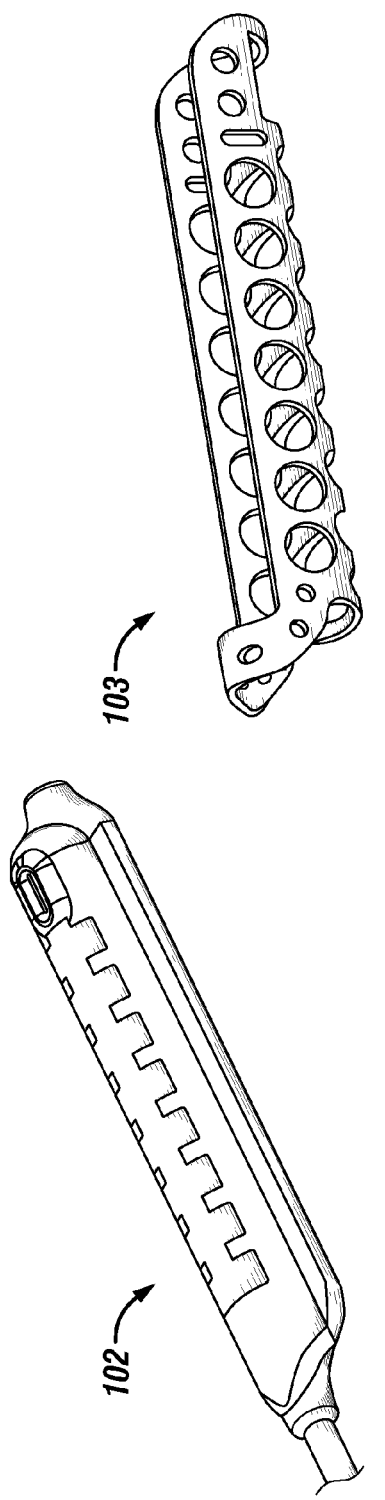
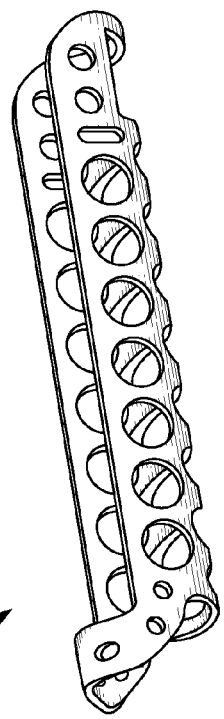
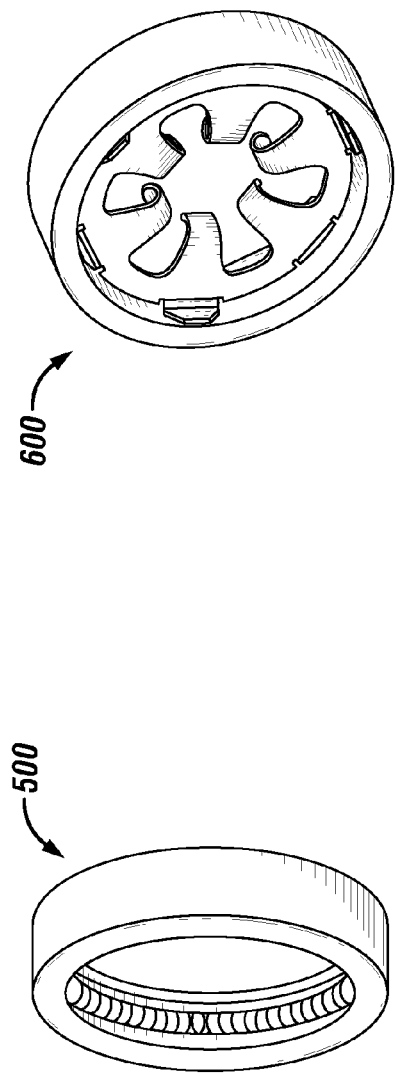
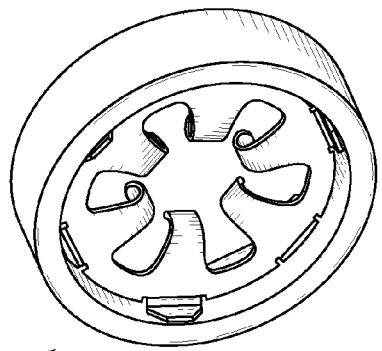
FIG. 4
FIG. 6
FIG. 3
FIG. 5

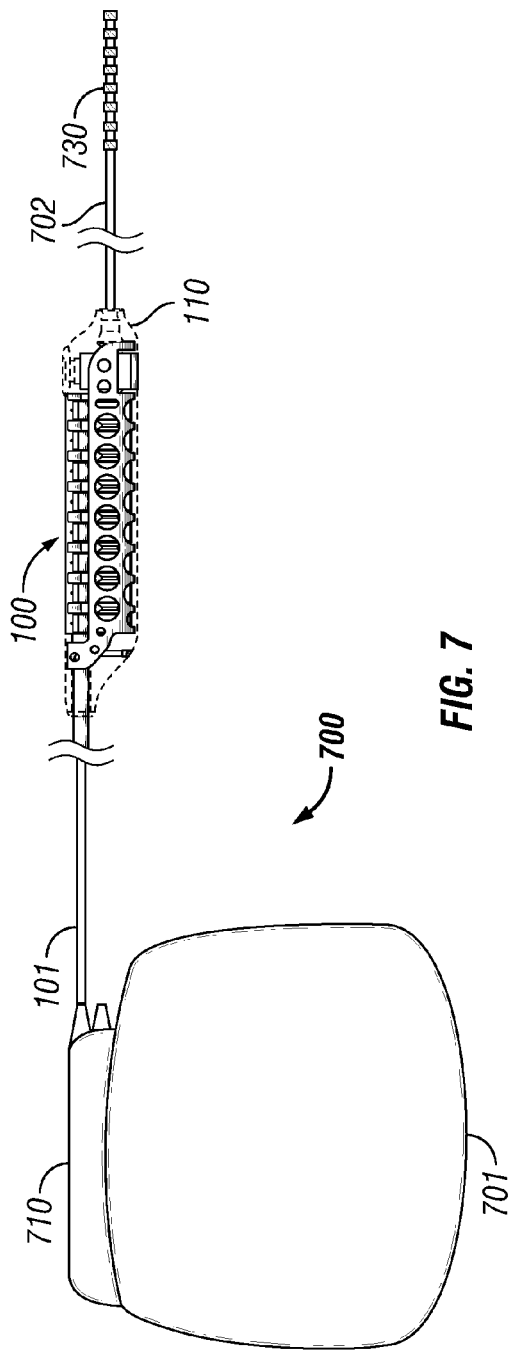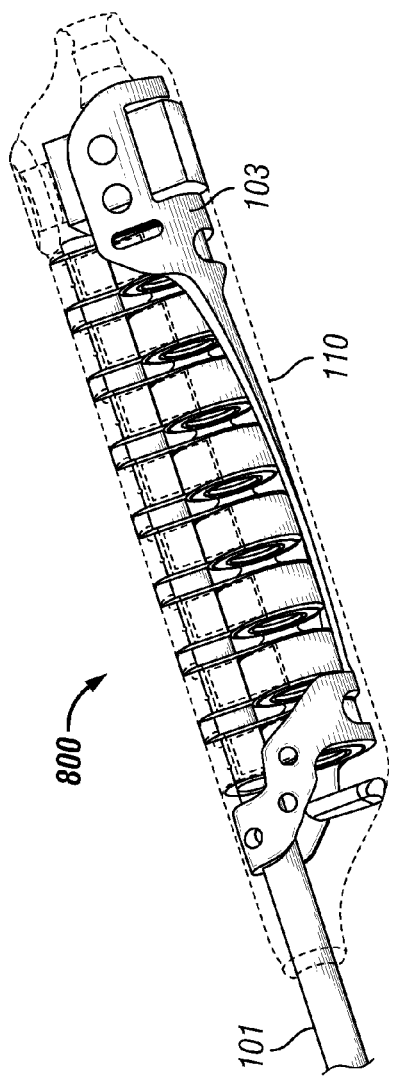

EXTENSION DEVICE FOR COUPLING BETWEEN PULSE GENERATOR AND STIMULATION LEAD, STIMULATION SYSTEM USING THE SAME, AND METHOD OF MANUFACTURING THE SAME

CROSS-REFERENCE TO RELATED APPLICATIONS

This application is claims the benefit of U.S. Provisional Application No. 60/978,592, filed Oct. 9, 2007, which is incorporated herein by reference.

BACKGROUND

The present application is generally related to a device for providing an electrical connection between an implantable pulse generator and one or more stimulation leads.

Neurostimulation systems are devices that generate electrical pulses and deliver the pulses to nerve tissue to treat a variety of disorders. Spinal cord stimulation (SCS) is an example of neurostimulation in which electrical pulses are delivered to nerve tissue in the spine, typically for the purpose of treating chronic pain. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Neurostimulation systems generally include a pulse generator and one or several leads. The pulse generator is typically implemented using a metallic housing that encloses circuitry for generating the electrical pulses. The pulse generator is usually implanted within a subcutaneous pocket created under the skin by a physician. The leads are used to conduct the electrical pulses from the implant site of the pulse generator to the targeted nerve tissue. The leads typically include a lead body of an insulative polymer material with embedded wire conductors extending through the lead body. Electrodes on a distal end of the lead body are coupled to the conductors to deliver the electrical pulses to the nerve tissue.

During an implantation procedure, there can be a relatively large distance between the implant site for the pulse generator and the stimulation site within the epidural space (depending upon the appropriate vertebral level for the patient's chronic pain). The distance may be greater than the length of a commercially available lead. To accommodate such circumstances, "lead extensions" may be employed to provide intermediate electrical connection between the pulse generator and the lead used to deliver stimulation pulses to patient tissue.

A lead extension is quite similar to a stimulation lead in some respects. A lead extension comprises a plurality of terminal electrical contacts on its proximal end that are electrically coupled to conductors within a lead body. Differing from stimulation leads, the distal end of a lead extension comprises a receptacle for providing electrical contacts. Specifically, the receptacle comprises a housing enclosing electrical connectors adapted to couple to the terminals of a stimulation lead. Each respective electrical connector is electrically coupled to a respective wire of the lead body.

Also, it is typical to utilize a somewhat lower durometer polymer for the housing of a lead extension. Specifically, the housing of the lead extension often can be disposed in a subcutaneous location that will apply pressure to the patient when the patient lies on the patient's back. Accordingly, an unduly hard material for the housing could cause a degree of discomfort for the patient.

BRIEF SUMMARY

In one embodiment, a lead extension comprises: a lead body; a plurality of conductors disposed within the lead body; a plurality of terminal contacts on a proximal end of the lead body, wherein the plurality of terminal contacts are electrically coupled to the plurality of conductors; and a housing structure disposed at a distal end of the lead body, the housing structure enclosing a plurality of electrical connectors for making electrical contact with terminal contacts of a stimulation lead, wherein the plurality of electrical connectors are electrically coupled to the plurality of conductors; the housing structure comprising an outer body of a first material and an inner reinforcing structure of a second material, wherein the first material is a relatively pliable biocompatible polymer material and the second material is a relatively rigid material, the reinforcing structure holding the plurality of electrical connectors in a relatively fixed arrangement.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE SEVERAL VIEWS OF THE DRAWING

FIG. 3 depicts an outer body of a lead extension in isolation according to one representative embodiment.

FIG. 4 depicts a reinforcing structure of a lead extension in isolation according to one representative embodiment.

FIGS. 5 and 6 depict known electrical connectors that may be employed with a lead extension according to one representative embodiment.

FIG. 7 depicts a stimulation system including a lead extension according to one representative embodiment.

FIG. 8 depicts a second lead extension according to another representative embodiment.

DETAILED DESCRIPTION

Figure 1:
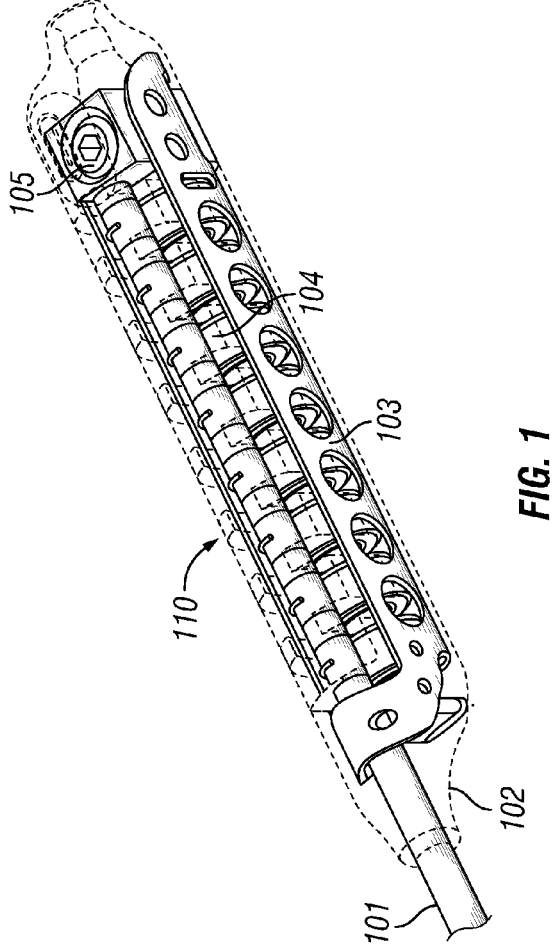
FIGS. 1 and 2 depict respective views of a lead extension according to one representative embodiment.

FIG. 1 depicts lead extension 100 according to one representative embodiment. Lead extension comprises lead body 101 which is coupled to housing structure 110. Lead body 101 may be implemented using any suitable lead design. In general, lead body 101 is typically implemented by disposing or embedding a plurality of conductors (not shown) within insulative material. The conductors can be wound in a helical manner along the length of the lead body 101 or disposed in a linear manner. In some embodiments, the insulative material is fused around each conductor. Terminal connectors (not shown) for coupling within the header of an implantable pulse generator are disposed on a proximal end of lead body 101.

Housing structure 110 comprises outer body 102. In one preferred embodiment, outer body 102 is fabricated using a pliable silicone material to provide a compliant outer surface for contact with patient tissue, although any lower durometer, biocompatible material could be alternatively selected. Because outer body 102 is relatively compliant, when pressure is applied to the patient tissue in the vicinity of housing structure 110, the patient does not experience undue discomfort.

To further enhance patient comfort and aid implantation, outer body 102 is also preferably fabricated using relatively smaller dimensions than typically employed by known lead extension devices. In one embodiment, housing structure 110 is approximately 1.34 inches (34.036 mm) long, has a width of approximately 0.18 inches (4.572 mm) and has thickness of approximately 0.236 inches (5.9944 mm). At such small dimensions, outer body 102 can be stretched or otherwise deformed by relatively low forces. For example, when a patient changes posture, lead body 101 may be subjected to stretching forces which are, in turn, transferred to outer body 102 thereby causing outer body 102 to stretch. Without adequate adaptation of housing structure 110, a stimulation lead placed within housing structure 110 would be displaced relative to electrical connectors 104. Accordingly, some or all terminals of the stimulation lead may lose electrical contact or be placed in electrical contact with an incorrect electrical connector 104.

Figure 2:
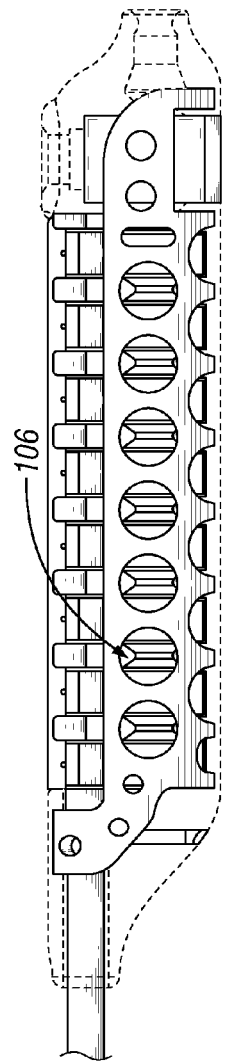

Some representative embodiments prevent stretching forces from disconnecting the electrical coupling with the stimulation lead by providing a reinforcing structure 103 within housing structure 110. Reinforcing structure 103 is preferably fabricated using a relatively higher durometer biocompatible polymer such polyetheretherketone (PEEK). Alternative designs could be employed for reinforcing structure 103 such as a thin wall of metal as an example. The relative mechanical strength of reinforcing structure 103 prevents reinforcing structure 103 from being deformed or stretched by forces commonly experienced after implantation. In one embodiment, one or more seals 106 can be likewise coupled to reinforcing structure 103. Electrical connectors 104 and locking mechanism 105 (e.g., a set-screw assembly) are disposed on reinforcing structure and are, thereby, held in a fixed arrangement relative to each other. Accordingly, when a stretching force is experience, the terminals of the stimulation lead are not dislocated relative to electrical connectors 104. Although housing structure 110 in the illustrated embodiment is adapted for use with a single stimulation lead, other embodiments may provide a plurality of electrical connectors in a side-by-side arrangement for use with multiple stimulation leads. An alternative view of lead extension 100 is shown in FIG. 2.

FIG. 3 depicts outer body 102 in isolation. Outer body 102 is preferably fabricated by molding over reinforcing structure 103, connectors 104, and any other internal components of housing structure 110. FIG. 4 depicts reinforcing structure 103 in isolation. Reinforcing structure 103 preferably possess a trough shape to hold the electrical connectors 104, although any suitable shape or design for holding the various components in a relatively fixed arrangement may be employed. For example, extension lead 800 (as shown in FIG. 8) utilizes a different shaped reinforcing structure 103 to provide a greater amount of flexibility for the housing structure 110 as a whole while providing sufficient rigidity to hold connectors 104 in a relatively fixed arrangement. For the purposes of this application, the phrase "in a relatively fixed arrangement" refers to holding the various components at substantially the same relative positions when forces typically experienced after implantation are applied to the structure. Also, the terms "relatively pliable" and "relatively rigid" refer to the mechanical characteristics of the outer body 102 relative to the mechanical characteristics of reinforcing structure 103 and vice versa.

Any known or later developed electrical connector may be used for electrical connectors 104. An example of a commercially available electrical connector is the BAL CONTACT™ electrical contact product available from Bal Seals, Inc. of Foothill Ranch, Calif. (see connector 500 in FIG. 5). An alternative electrical connector that may be employed is described in U.S. Patent Application Publication No. 20050107859, entitled "System and method of establishing an electrical connection between an implanted lead and an electrical contact" (see connector 600 in FIG. 6).

FIG. 7 depicts stimulation system 700 according to one representative embodiment. For the purpose of clearly illustrating each respective structure in FIG. 7, the various components are not shown in relative scale. Stimulation system 700 comprises pulse generator 701 which may be any commercially available pulse generator 701. An example of a suitable pulse generator is the EON® pulse generator available from Advanced Neuromodulation Systems, Inc. of Plano, Tex. Extension lead 100 is coupled within an aperture of header 710 of pulse generator 701. Stimulation lead 702 is inserted within the distal end of housing structure 110 of extension lead 100. Examples of suitable stimulation leads are the AXXESS® percutaneous lead and the LAMITRODE TRIPOLE 8™ paddle lead available from Advanced Neuromodulation Systems, Inc. of Plano, Tex. Electrical pulses from pulse generator 701 are conducted through the conductors of lead body 101, through the electrical connectors of extension lead 100, through the conductors of lead 702, and applied to tissue of the patient using electrodes 730 of lead 702.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

What is claimed:

1. A lead extension for providing intermediate electrical connection between an implantable pulse generator and one or more stimulation leads, comprising:

a lead body;

a plurality of conductors disposed within the lead body;
a plurality of terminal contacts on a proximal end of the lead body, wherein the plurality of terminal contacts are electrically coupled to the plurality of conductors; and
a housing structure disposed at a distal end of the lead body, the housing structure enclosing a plurality of electrical connectors for making electrical contact with terminal contacts of a stimulation lead, wherein the plurality of electrical connectors are electrically coupled to the plurality of conductors;
the housing structure comprising an outer body of a first material and an inner reinforcing structure of a second material, wherein the first material is a relatively pliable biocompatible polymer material and the second material is a relatively rigid material; and
the reinforcing structure including a U-shaped elongated body with a plurality of pair of holes along each side of the elongated body, the reinforcing structure for receiving therein a plurality of seals with each of the plurality of seals positioned intermediate one of a corresponding pair of holes of the U-shaped elongated body of the reinforcing structure.

2. The lead extension of claim 1 wherein the first material is a silicone-based material.

3. The lead extension of claim 1 wherein the second material is polyetheretherketone (PEEK).

4. The lead extension of claim 1 further comprising:
a lead locking mechanism for mechanically coupling to the stimulation lead.

5. The lead extension of claim 4 wherein the lead locking mechanism is held by the reinforcing structure.

6. The lead extension of claim 4 wherein the lead locking mechanism comprises a set-screw assembly for holding the stimulation lead.

7. The lead extension of claim 1 wherein the reinforcing structure forms a trough around the plurality of electrical connectors.

8. A stimulation system, comprising:
an implantable pulse generator;
a stimulation lead;
a lead extension that electrically couples the implantable pulse generator to the stimulation lead, the lead extension comprising:
a lead body;
a plurality of conductors disposed within the lead body;
a plurality of terminal contacts on a proximal end of the lead body for electrically coupling with the implantable pulse generator, wherein the plurality of terminal contacts are electrically coupled to the plurality of conductors; and
a housing structure disposed at a distal end of the lead body, the housing structure enclosing a plurality of electrical connectors for making electrical contact with terminal contacts of the stimulation lead, wherein the plurality of electrical connectors are electrically coupled to the plurality of conductors;
the housing structure comprising an outer body of a first material and an inner reinforcing structure of a second material, wherein the first material is a relatively pliable biocompatible polymer material and the second material is a relatively rigid material; and
the reinforcing structure including a U-shaped elongated body with a plurality of pair of holes along each side of the elongated body, the reinforcing structure for receiving therein a plurality of seals with each of the plurality of seals positioned intermediate one of a corresponding pair of holes of the U-shaped elongated body of the reinforcing structure.

9. The stimulation system of claim 8 wherein the first material is a silicone-based material.

10. The stimulation system of claim 8 wherein the second material is polyetheretherketone (PEEK).

11. The stimulation system of claim 8 further comprising:
a lead locking mechanism for mechanically coupling to the stimulation lead.

12. The stimulation system of claim 11 wherein the lead locking mechanism is held by the reinforcing structure.

13. The stimulation system of claim 11 wherein the lead locking mechanism comprises a set-screw assembly for holding the stimulation lead.

14. The stimulation system of claim 8 wherein the reinforcing structure forms a trough around the plurality of electrical connectors.

* * * * *